(12) United States Patent
Furuhashi et al.

(10) Patent No.: US 9,878,083 B2
(45) Date of Patent: Jan. 30, 2018

(54) BLOOD PURIFICATION APPARATUS WITH RECOGNITION AND CONTROL MEANS

(71) Applicant: Nikkiso Company Limited, Tokyo (JP)

(72) Inventors: Tomohiro Furuhashi, Shizuoka (JP); Satoshi Takeuchi, Shizuoka (JP); Akira Sugioka, Shizuoka (JP); Masahiro Toyoda, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 468 days.

(21) Appl. No.: 14/497,369

(22) Filed: Sep. 26, 2014

(65) Prior Publication Data

US 2015/0021244 A1 Jan. 22, 2015

Related U.S. Application Data

(63) Continuation of application No. PCT/JP2013/059367, filed on Mar. 28, 2013.

(30) Foreign Application Priority Data

Mar. 30, 2012 (JP) ................................ 2012-078922

(51) Int. Cl.
*B01J 49/00* (2017.01)
*A61M 1/16* (2006.01)
(Continued)

(52) U.S. Cl.
CPC ........ *A61M 1/1603* (2014.02); *A61M 1/1615* (2014.02); *A61M 1/342* (2013.01);
(Continued)

(58) Field of Classification Search
CPC ....... A61B 5/055; A61M 1/16; A61M 1/1603; A61M 1/1605; A61M 1/1615;
(Continued)

(56) References Cited

U.S. PATENT DOCUMENTS 418,565 A * 12/1889 St. John ................... B61G 3/04
213/109
2006/0079826 A1 4/2006 Beden et al.
(Continued)

FOREIGN PATENT DOCUMENTS

JP S60-153138 10/1985
JP 2004-016619 A 1/2004
(Continued)

OTHER PUBLICATIONS

Extended European Search Report, Application No. 13768746.3 dated Oct. 16, 2015.
(Continued)

*Primary Examiner* — Dirk Bass
*Assistant Examiner* — Hayden Brewster
(74) *Attorney, Agent, or Firm* — The Dobrusin Law Firm, P.C.

(57) ABSTRACT

A blood purification apparatus which can perform actions and operations according to the final stage of blood-return. Accordingly, a blood purification apparatus comprising a blood circuit including an arterial blood circuit and a venous blood circuit for extracorporeally circulating blood of a patient from a tip end of the arterial blood circuit to a tip end of the venous blood circuit; a blood purification means arranged between the arterial blood circuit and the venous blood circuit of the blood circuit and purifying blood flowing through the blood circuit; a substitution solution supplying means for supplying substitution solution to the blood circuit; and performing blood-return by substituting the blood in the blood circuit with the substitution solution supplied from the substitution solution supplying means after the blood purification treatment wherein the blood purification apparatus comprises a detecting means arranged at predetermined positions in the arterial blood circuit and (Continued)

the venous blood circuit and detecting presence or absence or blood concentration of the blood flowing in the arterial blood circuit and the venous blood circuit at said predetermined positrons, and a recognition means for recognizing a final stage of blood-return which is a condition near the end of the substitution of blood with the substitution solution based on the presence or absence of the blood or blood concentration detected by the detecting means.

20 Claims, 9 Drawing Sheets

(51) Int. Cl.
| | | |
|---|---|---|
| *A61M 1/34* | (2006.01) | |
| *B01D 11/00* | (2006.01) | |
| *B01D 61/00* | (2006.01) | |
| *C02F 1/44* | (2006.01) | |
| *A61M 1/36* | (2006.01) | |

(52) U.S. Cl.
CPC .......... *A61M 1/3458* (2014.02); *A61M 1/367* (2013.01); *A61M 1/3646* (2014.02); *A61M 1/3626* (2013.01); *A61M 2202/0413* (2013.01); *A61M 2205/331* (2013.01); *A61M 2205/3306* (2013.01); *A61M 2205/75* (2013.01)

(58) Field of Classification Search
CPC .. A61M 1/1654; A61M 1/1656; A61M 1/342; A61M 1/36; A61M 1/367; A61M 1/3609; A61M 1/3626; A61M 1/3643; A61M 1/3646; A61M 2001/165; A61M 2001/3437; A61M 2202/0413; A61M 2205/12; A61M 2205/331; A61M 2205/3306; A61M 2205/75; A61M 2230/20; B01D 35/00; B01D 35/143; B01D 61/12; C02F 1/003; C02F 1/008; C02F 1/325; G01R 13/04; G01R 23/00; G01R 23/16; G01R 23/165; G01R 23/173; G01R 27/28; G01R 31/265; G01R 31/303; G01R 31/2656; G01R 31/3025; G01R 33/20; G01R 33/28; G01R 33/30; G01R 33/46; G01R 33/302; G01R 33/307; G01R 33/341; G01R 33/383; G01R 33/385; G01R 33/389; G01R 33/421; G01R 33/465; G01R 33/583; G01R 33/3415; G01R 33/3621; G01R 33/3628; G01R 33/3635; G01R 33/3806; G01R 33/3815; G01R 33/3852; G01R 33/3873; G01R 33/3875; G01R 33/34046; G01R 33/34053; G01R 33/34092; G01V 11/002; H03F 1/3211; H03E 2200/294; H03E 2200/372; H03H 7/0161; H03J 1/0083; H03J 5/242; H03J 5/244; H04B 1/005; H04B 1/18; H04B 1/26; H04B 1/30; H04B 1/40; H04B 1/44; H04B 1/54; H04B 1/406; H04B 1/3822; H04M 1/7253; H04M 2250/02; H04W 76/02; H04W 84/18; H04W 88/06

USPC .............. 73/861.11; 210/85, 96.2, 646, 647; 324/76.19, 113, 313, 318–322, 754.31; 340/854.6

See application file for complete search history.

(56) References Cited

U.S. PATENT DOCUMENTS

| | | | |
|---|---|---|---|
| 2009/0024070 A1* | 1/2009 | Gelfand ................. | A61M 1/34 604/6.09 |
| 2010/0274172 A1* | 10/2010 | Guenther .............. | A61M 1/342 604/6.11 |
| 2011/0139690 A1* | 6/2011 | Akita ..................... | G01N 21/05 210/96.1 |
| 2012/0000547 A1 | 1/2012 | Gronau et al. | |

FOREIGN PATENT DOCUMENTS

| | | |
|---|---|---|
| JP | 2006-280775 A | 10/2006 |
| JP | 2007-007435 A | 1/2007 |
| JP | 2007-167108 A | 7/2007 |
| JP | 2009-112651 A | 5/2009 |
| JP | 2009-131412 A | 6/2009 |
| JP | 2010-273784 | 12/2009 |
| JP | 2010-269050 A | 12/2010 |

OTHER PUBLICATIONS

Translation of International Search Report Application No. PCT/JP2012/072976, dated Dec. 4, 2012.

* cited by examiner

[FIG 1]
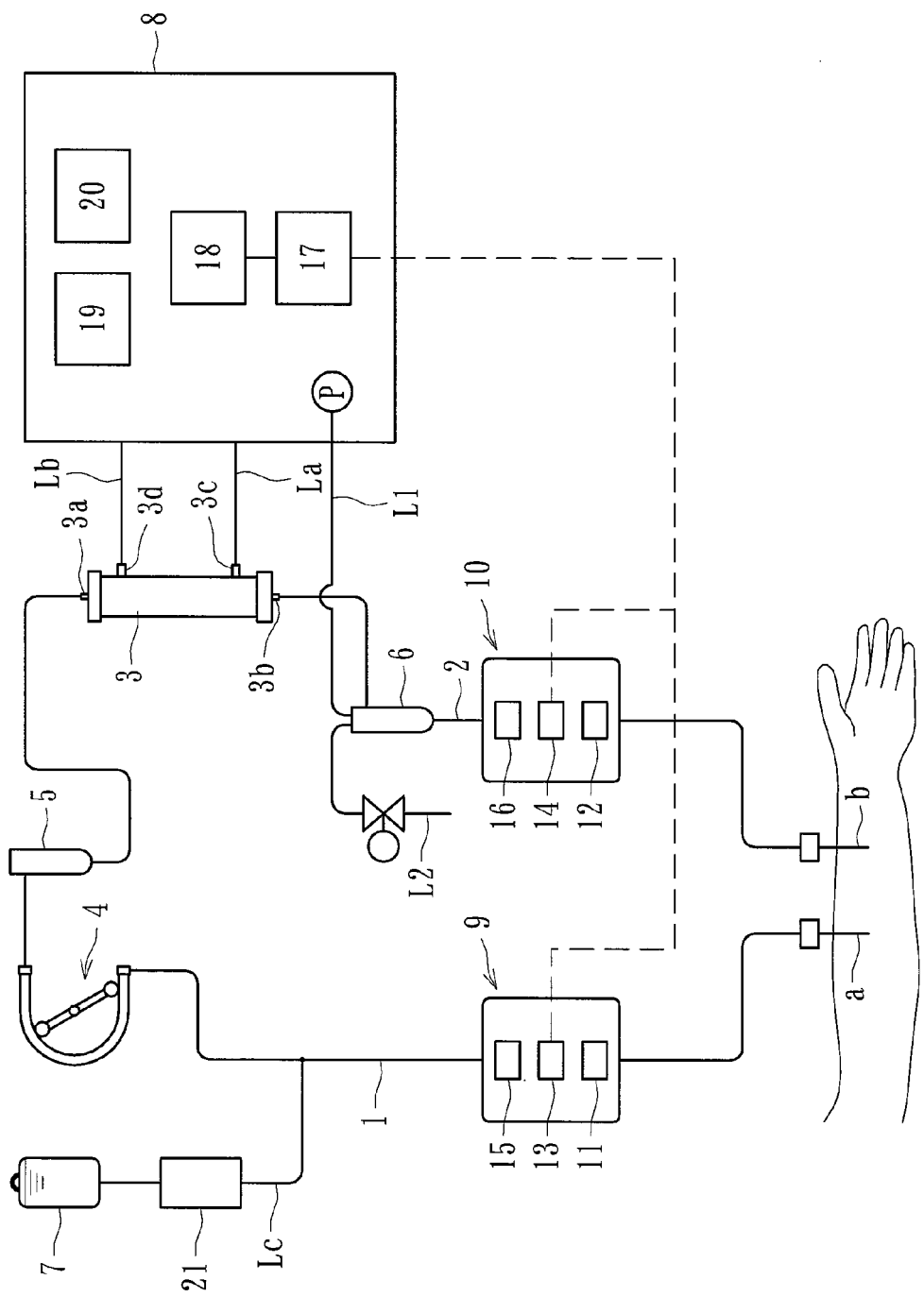

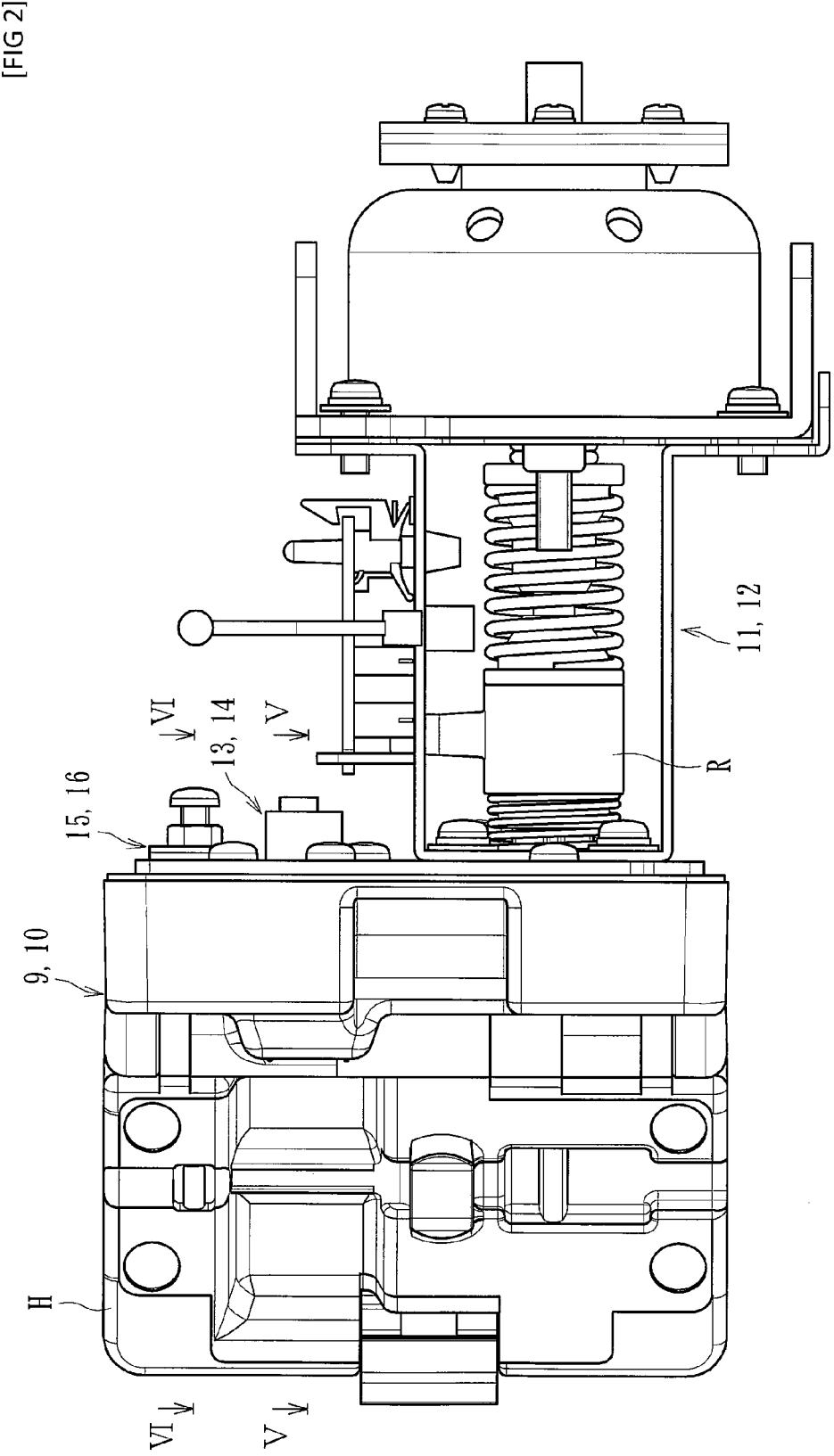
[FIG 2]

[FIG 3]
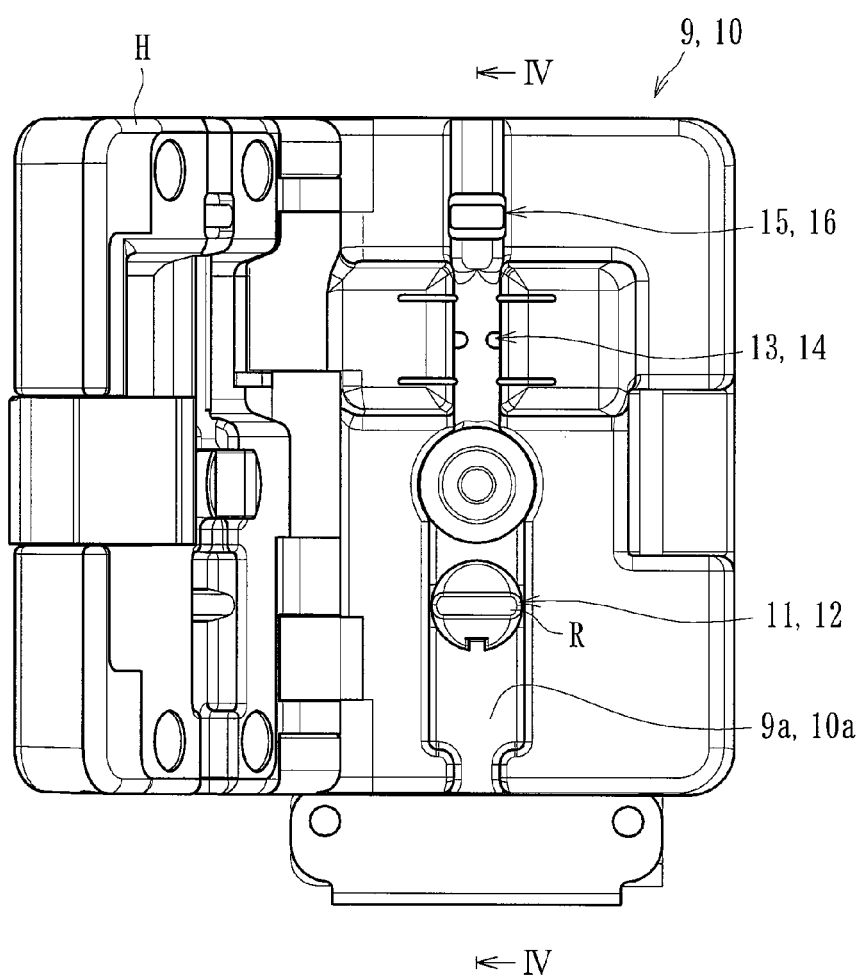

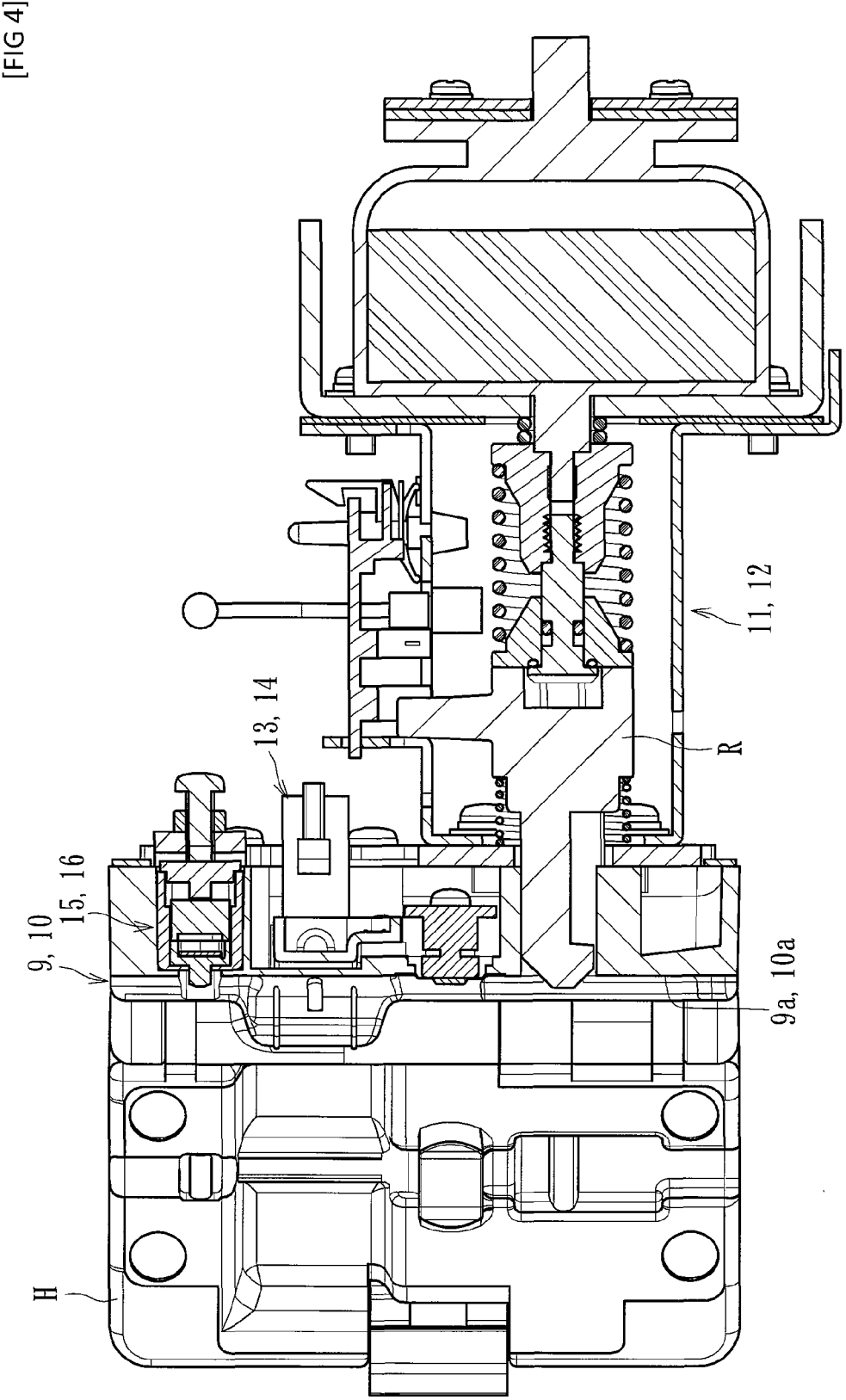

[FIG 5]
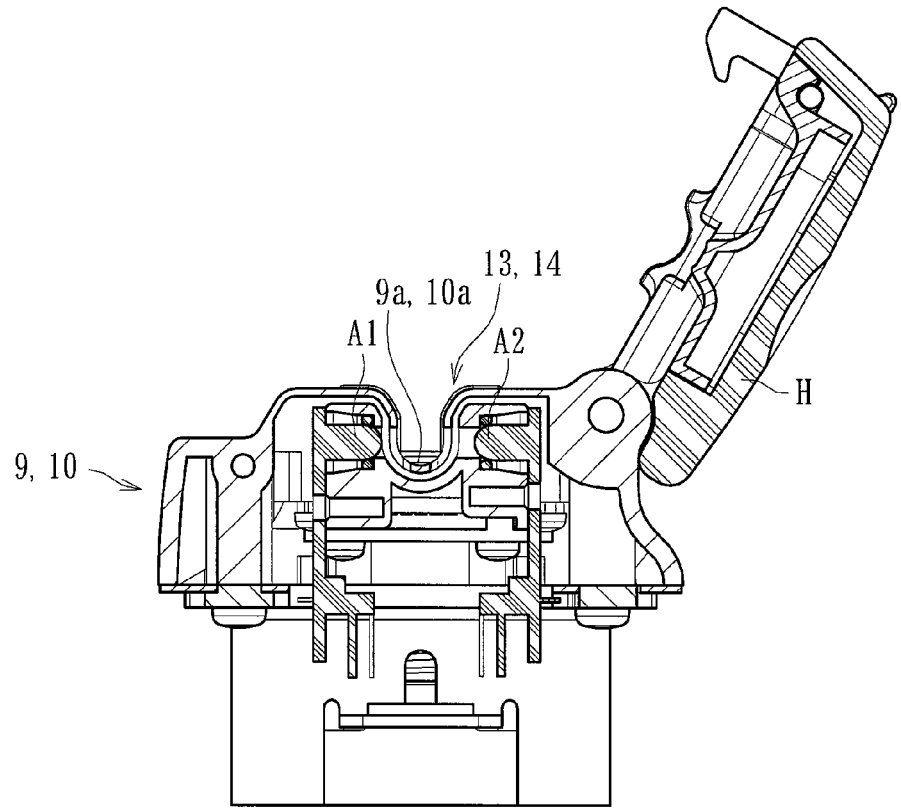
[FIG 6]
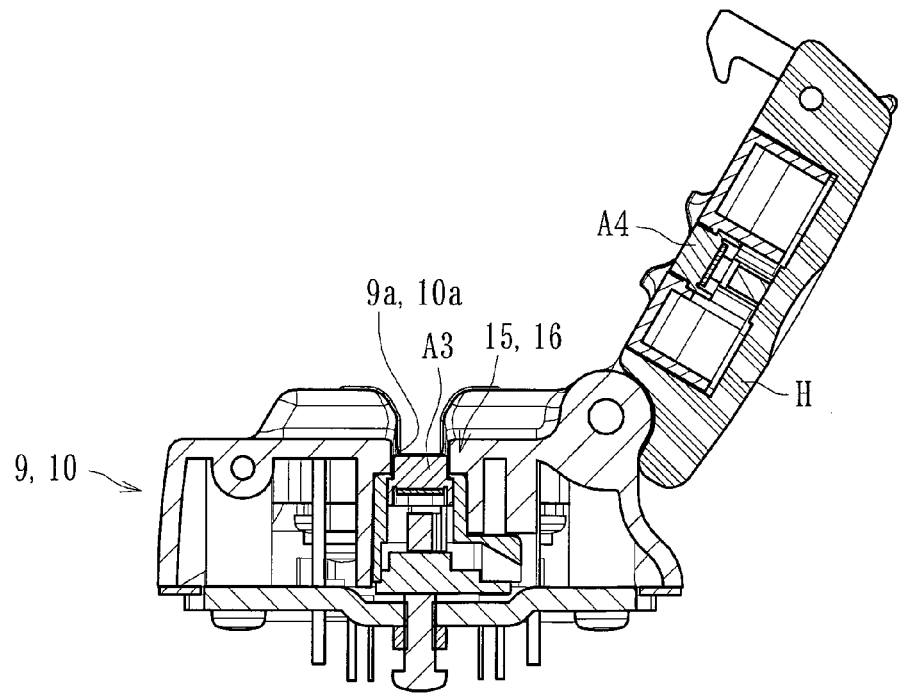

[FIG 7]
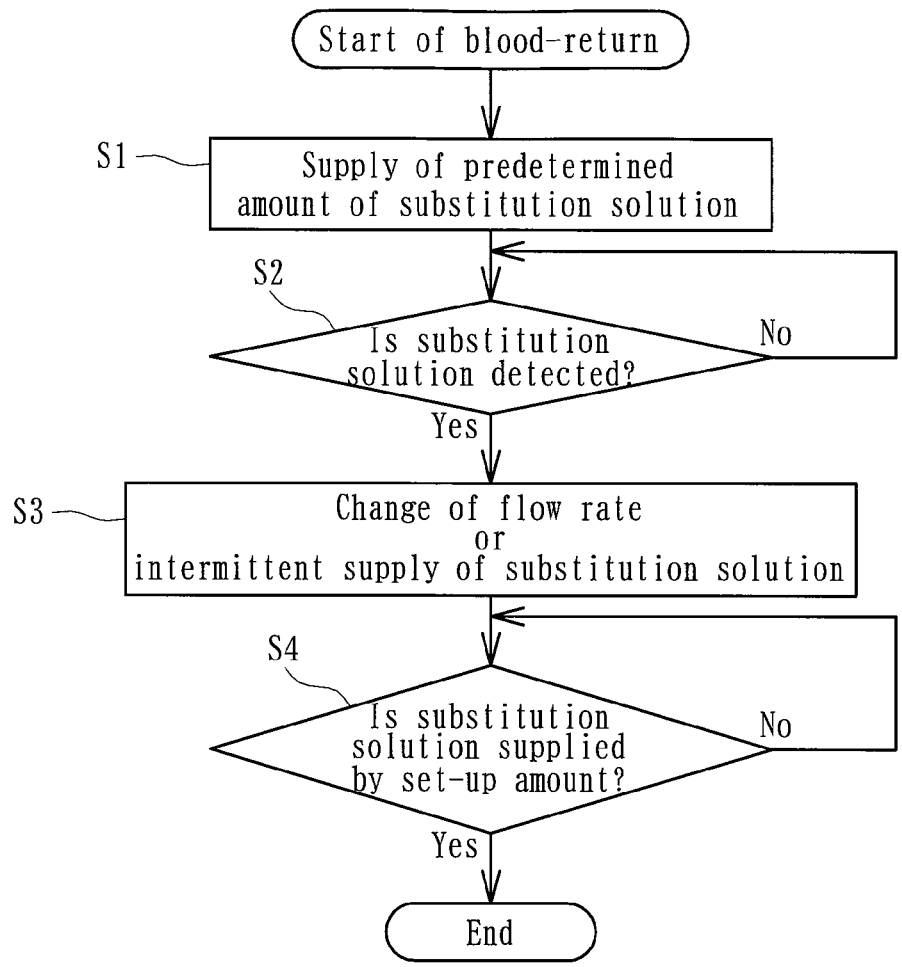

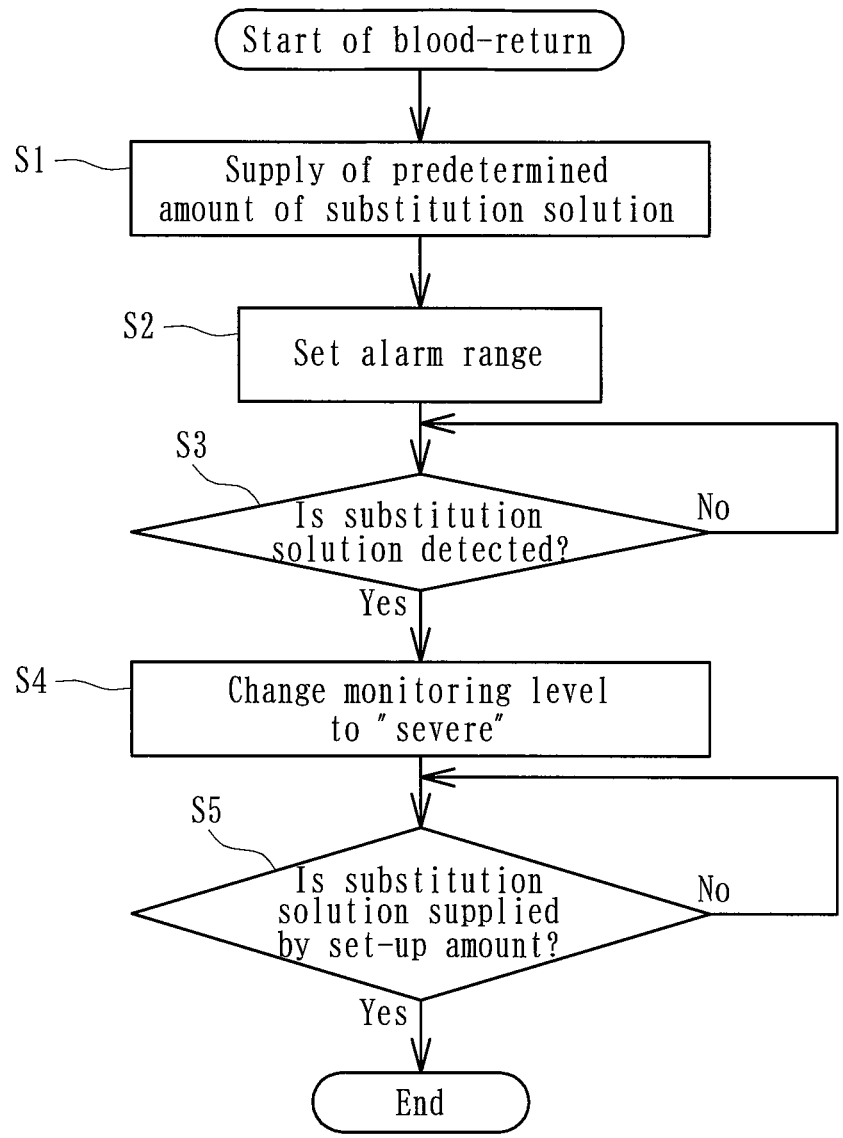

[FIG 9]
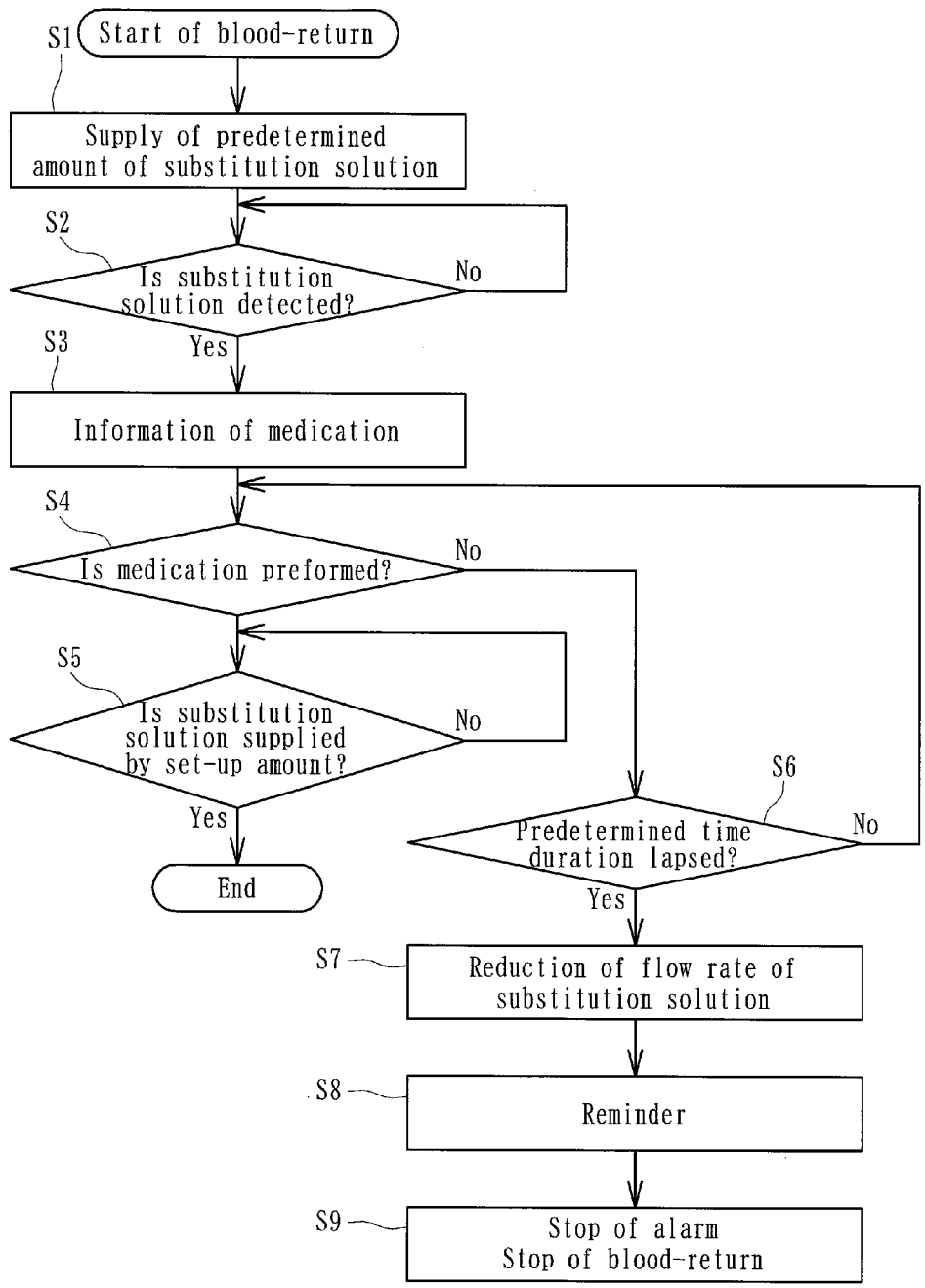

[FIG 10]
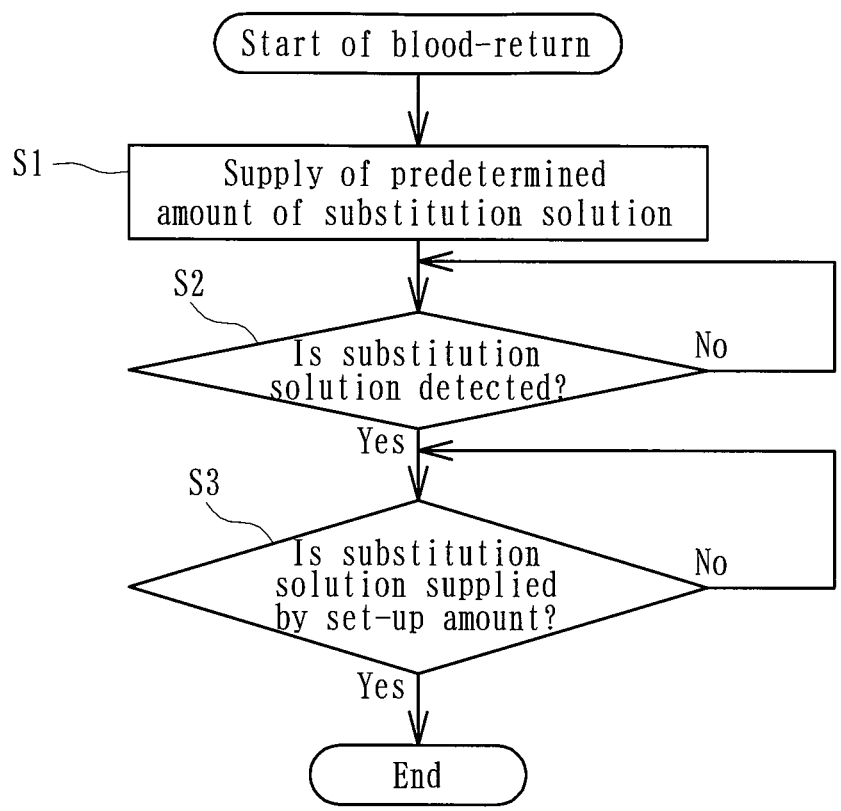

BLOOD PURIFICATION APPARATUS WITH RECOGNITION AND CONTROL MEANS

FIELD

The present invention relates to a blood purification apparatus for extracorporeally circulating blood of a patient used in the dialysis treatment using a dialyzer.

DESCRIPTION OF BACKGROUND ART

In general, it is used in the dialysis treatment a blood circuit for extracorporeally circulating collected blood of a patient and returning it again to a body of a patient. The blood circuit mainly comprises an arterial blood circuit and a venous blood circuit to be connected to a dialyzer (blood purification means) provided with a hollow fiber membrane. Puncture needles are adapted to be mounted on tip ends of the arterial blood circuit and the venous blood circuit to perform the extracorporeally blood circulation in the dialysis treatment with the puncture needles being punctured to a patient.

After completion of the dialysis treatment, a blood-returning operation for returning blood remained in the blood circuit, dialyzer, arterial air-trap chamber, venous air-trap chamber etc to a patient is required. In such a blood-returning operation of the prior art, the blood in the blood circuit has been substituted with physiological saline (substitution solution) by introducing the physiological saline in the middle of the arterial blood circuit as disclosed e.g. in Patent Document 1 below.

It is performed in the prior art to make automation of the blood-return operation easy as disclosed in Patent Document 2 to return blood in the blood circuit and dialyzer to a body of patient through the arterial puncture needle and the venous puncture needle by rotating a blood pump reversely to the rotation in the dialysis treatment with inversely filtrating the dialysate (substituting solution) from a dialysate flow path to a blood flow path and by substituting the blood remained in the blood circuit with the inversely filtrated dialysate.

DOCUMENT OF PRIOR ART

Patent Documents

Patent Document 1: JP 2006-280775 A; Patent Document 2. JP 2009-131412 A

DISCLOSURE OF THE INVENTION

Problems to be Solved by the Invention

However, in the blood purification apparatus of the prior art described above, since the supply of substitution solution and its associated actions or operations are uniformly performed over whole blood-return in every facilities, it is impossible to perform actions or operations according to the degree of progress of the blood substitution in individual patients and thus problems such as increase of use of the substitution solution or increase of on-duty hours of a patient by dialysis of patients would be caused.

That is, the substitution solution sometimes stays in an enlarged portion of the air-trap chamber connected to the blood circuit or branched flow paths or connected portions to dialyzer (blood purification means) during supply of the substitution solution in the blood-return process and thus it is necessary to somewhat increase supply of the substitution solution. This increase of the substitution solution causes the problems of the prior art, i.e. the increase of use of the substitution solution or increase of on-duty hours of a patient by dialysis.

In recent years, desire for automation of the blood-return has been increased and thus it is very important to control the supply of substitution solution and its associated actions or operations according to the degree of progress of the blood substitution. Especially in the final stage of blood-return, although it is necessary to have actions and operations different from those in the start stage of blood-return, the blood purification apparatus of the prior art cannot grasp the degree of progress of blood-return and the final stage of blood-return.

It is, therefore, an object of the present invention to provide a blood purification apparatus which can perform actions and operations according to the final stage of blood-return.

Means for Solving the Problems

For achieving the object of the present invention, there is provided according to the present invention; a blood purification apparatus comprising a blood circuit including an arterial blood circuit and a venous blood circuit for extracorporeally circulating blood of a patient from a tip end of the arterial blood circuit to a tip end of the venous blood circuit; a blood purification means arranged between the arterial blood circuit and the venous blood circuit of the blood circuit and purifying blood flowing through the blood circuit; a substitution solution supplying means for supplying substitution solution to the blood circuit; and performing blood-return by substituting the blood in the blood circuit with the substitution solution supplied from the substitution solution supplying means after the blood purification treatment characterized in that the blood purification apparatus further comprises a detecting means arranged at predetermined positions in the arterial blood circuit and the venous blood circuit and detecting presence or absence or blood concentration of the blood flowing in the arterial blood circuit and the venous blood circuit at said predetermined positions, and a recognition means for recognize a final stage of blood-return which is a condition near the end of the substitution of blood with the substitution solution based on the presence or absence of the blood or blood concentration detected by the detecting means.

According to the present invention of the teachings herein, there is provided a blood purification apparatus as is taught herein, wherein the blood purification apparatus further comprises a control means for performing predetermined controls concerning to actions or operations carried out at the final stage of blood return subject to the recognition of the final stage of blood-return by the recognition means.

According to the present invention of the teachings herein, there is provided a blood purification apparatus as taught herein, wherein the control means can increase or decrease a supplying flow rate of the substitution solution by the substitution solution supplying means subject to the recognition of the final stage of blood-return by the recognition means.

According to the present invention of the teachings herein, there is provided a blood purification apparatus as taught herein, wherein the control means can intermittently perform the supply of the substitution solution by the substitution solution supplying means subject to the recognition of the final stage of blood-return by the recognition means.

According to the present invention of the teachings herein, there is provided a blood purification apparatus as taught herein, wherein the control means can perform the supply of the substitution solution by the substitution solution supplying means by a set-up amount depending on the arranged position of the detecting means subject to the recognition of the final stage of blood-return by the recognition means.

According to the present invention of the teachings herein, there is provided a blood purification apparatus as taught herein, wherein the blood purification apparatus further comprises a monitoring means for monitoring abnormalities during the blood-return, and wherein the control means can make the abnormality monitoring by the monitoring means severe subject to the recognition of the final stage of blood-return by the recognition means.

According to the present invention of the teachings herein, there is provided a blood purification apparatus as taught herein, wherein the control means can perform information that a predetermined medical treatment should be performed to a patient subject to the recognition of the final stage of blood-return by the recognition means.

According to the present invention of the teachings herein, there is provided a blood purification apparatus as is taught herein, wherein the predetermined medical treatment is medication to a patient.

According to the present invention as taught herein, there is provided a blood purification apparatus of the teachings herein, wherein the detecting means is a blood discriminating means which is arranged at predetermined positions in tip end sides of the arterial blood circuit and the venous blood circuit and can discriminate presence or absence of the blood flowing in the arterial blood circuit and the venous blood circuit at said predetermined positions.

According to the present invention of the teachings herein, there is provided a blood purification apparatus as taught herein, wherein the detecting means comprises a concentration sensor which can detect the blood concentration of the blood flowing in the arterial blood circuit and the venous blood circuit at said predetermined positions, and wherein the recognition means can recognize the final stage of blood-return with grasping a state of progress of the substitution by the substitution solution based on the blood concentration detected by the concentration sensor.

According to the present invention of the teachings herein, there is provided a blood purification apparatus as taught herein, wherein the recognition means can recognize an early stage of blood-return in addition to the final stage of blood-return based on the blood concentration detected by the concentration sensor, and wherein the supplying flow rate of the substitution solution supplied by the substitution solution supplying means is set larger in the early stage of blood-return than the supplying flow rate in the final stage of blood-return.

Effects of the Invention

According to the present inventions of the teachings herein, since the blood purification apparatus comprises a detecting means arranged at predetermined positions in the arterial blood circuit and the venous blood circuit and detecting presence or absence or blood concentration of the blood flowing in the arterial blood circuit and the venous blood circuit at said predetermined positions, and a recognition means for recognize a final stage of blood-return which is a condition near the end of the substitution of blood with the substitution solution based on the presence or absence of the blood or blood concentration detected by the detecting means, it is possible to perform actions and operations according to the final stage of blood-stage.

According to the present invention of the teachings herein, since the blood purification apparatus comprises a control means for performing predetermined controls concerning to actions or operations carried out at the final stage of blood-return subject to the recognition of the final stage of blood-return by the recognition means, it is possible to automatically perform actions and operations according to final stage of the blood-return.

According to the present invention of the teachings herein, since the control means can increase or decrease a supplying flow rate of the substitution solution by the substitution solution supplying means subject to the recognition of the final stage of blood-return by the recognition means, it is possible to make the supplying flow rate of the substitution solution suitable for the final stage of blood-return.

According to the present invention of the teachings herein, since the control means can intermittently perform the supply of the substitution solution by the substitution solution supplying means subject to the recognition of the final stage of blood return by the recognition means, it is possible to suppress thrombus or air-bubbles stayed in the blood circuit from being carried to a body of patient.

According to the present invention of the teachings herein, since the control means can perform the supply of the substitution solution by the substitution solution supplying means by a set-up amount depending on the arranged position of the detecting means subject to the recognition of the final stage of blood-return by the recognition means, it is possible to reduce use of the substitution solution.

According to the present invention of the teachings herein, since the blood purification apparatus further comprises a monitoring means for monitoring abnormalities during the blood-return, and the control means can make the abnormality monitoring by the monitoring means severe subject to the recognition of the final stage of blood-return by the recognition means, it is possible to more surely suppress thrombus or air-bubbles stayed in the blood circuit from being carried to a body of patient.

According to the present invention of the teachings herein, since the control means can perform information that a predetermined medical treatment should be performed to a patient subject to the recognition of the final stage of blood-return by the recognition means, it is possible to prevent that medical workers forget predetermined medical treatments to be performed at the final stage of blood-return and thus possible to surely perform necessary medical treatments.

According to the present invention of the teachings herein, since the predetermined medical treatment is medication to a patient, it is possible to prevent that medical workers forget medication (dosing) to be performed at the final stage of blood-return and thus possible to surely perform necessary medication.

According to the present invention of the teachings herein, since the detecting means is a blood discriminating means which is arranged at predetermined positions in tip end sides of the arterial blood circuit and the venous blood circuit and can discriminate presence or absence of the blood flowing in the arterial blood circuit and the venous blood circuit at said predetermined positions, it is possible to divert the blood discriminating means used during medical treatment to the detecting means.

According to the present invention of the teachings herein, since the detecting means comprises a concentration sensor which can detect the blood concentration of the blood flowing in the arterial blood circuit and the venous blood circuit at said predetermined positions, and the recognition means can recognize the final stage of blood-return with grasping a state of progress of the substitution by the substitution solution based on the blood concentration detected by the concentration sensor, it is possible to perform a stepwise control according to the degree of progress of blood-return.

According to the present invention of the teachings herein, since the recognition means can recognize an early stage of blood-return in addition to the final stage of blood-return based on the blood concentration detected by the concentration sensor, and the supplying flow rate of the substitution solution supplied by the substitution solution supplying means is set larger in the early stage of blood-return than the supplying flow rate in the final stage of blood-return, it is possible to reduce the time for blood-return and to suppress sudden elevation of blood pressure of a patient.

BRIEF DESCRIPTION OF THE DRAWINGS

FIG. 1 A general schematic view showing a blood purification apparatus of a first embodiment of the present invention;

FIG. 2 A side elevation view showing a detecting means (blood discriminating means) of the blood purification apparatus of FIG. 1;

FIG. 3 A front elevation view of the detecting means of FIG. 2;

FIG. 4 A cross-sectional view taken along a line IV-IV of FIG. 3;

FIG. 5 A cross-sectional view taken along a line V-V of FIG. 2;

FIG. 6 A cross-sectional view taken along a line VI-VI of FIG. 2;

FIG. 7 A flow chart showing the control of the blood purification apparatus of FIG. 1;

FIG. 8 A flow chart showing the control of the blood purification apparatus of a second embodiment of the present invention;

FIG. 9 A flow chart showing the control of the blood purification apparatus of a third embodiment of the present invention; and FIG. 10 A flow chart showing the control of the blood purification apparatus of a fourth embodiment of the present invention.

DESCRIPTION OF EMBODIMENTS

The present teachings claim priority to Japanese Patent No. 2012-078922 filed on Mar. 30, 2012 and International Patent Application No PCT/JP2013/059367, filed on Mar. 28, 2013 both of which are expressly incorporated by reference herein for all purposes. Preferable embodiments of the present invention will be hereinafter described with reference to the drawings. As shown in FIG. 1, the blood purification apparatus of the first embodiment including a dialysis apparatus for performing dialysis treatment mainly comprises a blood circuit including an arterial blood circuit 1 and a venous blood circuit 2; a dialyzer (blood purification means) 3 arranged between the arterial blood circuit 1 and the venous blood circuit 2 of the blood circuit and purifying blood flowing through the blood circuit; a peristaltic blood pump 4 arranged on the arterial blood circuit 1; an arterial air-trap chamber 5 and a venous air-trap chamber 6 arranged respectively on the arterial blood circuit 1 and the venous blood circuit 2; a main body 8 of the dialysis apparatus for supplying dialysate to the dialyzer 3; a saline bag 7 and a substitution solution supplying line Lc forming a substitution solution supplying means; blood discriminating means 13, 14 forming a blood detecting means; a recognition means 17; and a control means 18.

An arterial puncture needle "a" is connected to a tip end of the arterial blood circuit 1 and a peristaltic blood pump 4 and an arterial air-trap chamber 5 are arranged in the middle of the arterial blood circuit 1. On the other hand, a venous puncture needle "b" is connected to a tip end of the venous blood circuit 2 and a venous air-trap chamber 6 is arranged in the middle of the venous blood circuit 2. Each of the arterial air-trap chamber 5 and the venous air-trap chamber 6 contains therein filtration nets (not shown) for catching thrombus etc. during the blood-return process. The arterial air-trap chamber 5 is arranged between the blood pump 4 and the dialyzer 3 in the arterial blood circuit 1.

When the blood pump 4 is driven under a condition in which the arterial puncture needle "a" and the venous puncture needle "b" are punctured to a patient, blood of a patient flows to the dialyzer 3 through the arterial blood circuit 1, is purified by the dialyzer 3 and finally returned to a body of a patient through the venous blood circuit 2 with bubbles being removed by the venous air-trap chamber 6. That is, blood of a patient can be purified by the dialyzer 3 with being extracorporeally circulated from the tip end "a" of the arterial blood circuit 1 to the tip end "b" of the venous blood circuit 2.

The dialyzer 3 is formed on its casing with a blood introducing port 3a, a blood discharging port 3b, a dialysate introducing port 3c and a dialysate discharging port 3d, and a base end of the arterial blood circuit 1 is connected to the blood introducing port 3a and a base end of the of the venous blood circuit 2 is connected to the blood discharging port 3b. Furthermore, the dialysate introducing port 3c and the dialysate discharging port 3d are connected respectively to a dialysate introducing line La and a dialysate discharging line Lb extending from the main body 8 of the dialysis apparatus.

A large number of hollow fibers are contained in the dialyzer 3 and a blood flow path is formed in each hollow fiber and a dialysate flow path is formed between the inner circumference of the casing of the dialyzer 3 and the outer circumference of each hollow fiber. Each hollow fiber is formed with a vast number of micro-pores passing through between the outer circumference and the inner circumference to form a hollow fiber membrane. Accordingly, impurities in blood can be permeated into the dialysate through the hollow fiber membrane.

On the other hand, an ultrafiltration pump (not shown) for removing water content from blood of a patient flowing through the dialyzer 3 is arranged within the main body 8 of the dialysis apparatus. One end of the dialysate introducing line La is connected to the dialyzer 3 (dialysate introducing port 3c) as described above, and the other end thereof is connected to a dialysate supplying apparatus (not shown) for preparing dialysate of predetermined concentration. One end of the dialysate discharging line Lb is connected to the dialyzer 3 (dialysate discharging port 3d) as described above, and the other end thereof is connected to a dialysate wasting apparatus (not shown). Accordingly, the dialysate supplied from the dialysate supplying apparatus by driving dialysate supplying means (not shown) is supplied to the dialyzer 3 through the dialysate introducing line La and finally sent to the dialysate wasting means through the dialysate discharging line Lb.

A monitoring tube L1 extends from an upper portion (air layer side) of the venous air-trap chamber 6 and a tip end of the monitoring tube L1 is connected to a pressure sensor P within the main body 8 of the dialysis apparatus. The pressure sensor P can detect a liquid pressure (venous pressure) within the venous air-trap chamber 6. An overflow line L2 is also extends from the upper portion (air layer side) of the venous air trap chamber 6 to overflow priming liquid during priming process before the dialysis treatment.

The substitution solution supplying means comprising the saline bag 7 and the substitution solution supplying line Lc can supply substitution solution (physiological saline) to the blood circuit. The saline bag 7 formed of flexible clear container for a predetermined amount of physiological saline is adapted to be suspended on a tip end of a pole projected from the main body 8 of the dialysis apparatus. The substitution solution supplying line Lc is connected to a portion of the arterial blood circuit 1 between the tip end (on which the arterial puncture needle "at" is mounted) and the blood pump 4 and able to supply the physiological saline (substitution solution) contained within the saline bag 7 to the blood circuit.

An opening closing means 21 for opening and closing the flow path of the substitution solution supplying line Lc is arranged in the middle of the substitution solution supplying line Lc. The opening/closing means 21 comprises an electromagnetic valve such as electromagnetic valves 11, 12 later described and is controlled by a control means 18 within the main body 8 of the dialysis apparatus. It may be used for the opening/closing means 21 in place of the electromagnetic valve any manually operable conventional means for opening and closing the substitution solution supplying line Lc.

The physiological saline (substitution solution) within the saline bag 7 will be supplied, by its own weight to the arterial blood circuit 1 through the substitution solution supplying line Lc when the opening/closing means 21 is opened, and the supplied physiological saline can be further supplied to the tip end "a" of the arterial blood circuit 1 or the tip end "b" of the venous blood circuit 2 by driving the blood pump 4 to a normal direction or a reverse direction to sequentially substitute blood in the blood circuit (i.e. arterial blood circuit 1 and venous blood circuit 2) with the physiological saline.

According to the present, an arterial unit 9 comprising the electromagnetic valve 11, the blood discriminating means (blood detecting means) 13 and an air-bubble detecting means 15 is arranged on a predetermined position in the tip end side of the arterial blood circuit 1, and a venous unit 10 comprising the electromagnetic valve 12, the blood discriminating means (blood detecting means) 14 and an air-bubble detecting means 16 is arranged on a predetermined position in the tip end side of the venous blood circuit 2. The arterial unit 9 and the venous unit 10 are structured as shown in FIGS. 2 to 6 so that flexible tubes forming the arterial blood circuit 1 and the venous blood circuit 2 fitted in fitting grooves 9a, 10a can be sandwiched between the fitting grooves 9a, 10a and a lid member H by closing the lid member H relative to the fitting grooves 9a, 10a.

The electromagnetic valves 11, 12, the blood discriminating means 13, 14 and the air-bubble detecting means 15, 16 are arranged by this order from the tip-end sides of the arterial blood circuit 1 and the venous blood circuit 2 respectively along the fitting grooves 9a, 10a of the arterial unit 9 and the venous unit 10. The electromagnetic valves 11, 12 can open and close predetermined flow paths of the tip-end sides respectively of the arterial blood circuit 1 and the venous blood circuit 2 by their opening and closing operations which are controlled by the control means 18 within the main body 8 of the dialysis apparatus. A reference character "R" in FIG. 4 denotes push rods of the electromagnetic valves 11, 12 which can open and close the predetermined flow paths with being advanced and retracted.

Each of the blood discriminating means 13, 14 as the blood detecting means is formed by a discriminating sensor being able to discriminate presence or absence of blood flowing in the arterial blood circuit 1 and the venous blood circuit 2 at positions (predetermined positions) in which the arterial unit 9 and the venous unit 10 are arranged, and comprises as shown in FIG. 5 a light emitting element A1 and a light receiving element A2 formed by e.g. LEDs. These light emitting element A1 and light receiving element A2 are arranged in right and left across the fitting groove 9a, 10a so that the light irradiated on flexible tubes forming the arterial blood circuit 1 and the venous blood circuit 2 by the light emitting element A1 can be received by the light receiving element A2.

The light receiving element A2 can vary an output voltage according to its light income and discriminate presence or absence of blood flowing in the arterial blood circuit 1 and the venous blood circuit 2 according to the detected output voltage. That is, since the transmissivity of light of the substitution solution (physiological saline in the present embodiment) is higher than that of the blood, a fact that a voltage detected by the light receiving element A2 exceeds a predetermined threshold means that liquid flowing in the blood circuit 1 or 2 has been substituted by the substitution solution from blood.

The air-bubble detecting means 15, 16 is formed by a sensor which can detect air (air-bubble) flowing in the arterial blood circuit 1 and the venous blood circuit 2 at positions (predetermined positions) in which the arterial unit 9 and the venous unit 10 are arranged, and comprises as shown in FIG. 6 an ultrasonic vibration element A3 and ultrasonic vibration receiving element A4 both being formed e.g. by piezoelectric elements. The ultrasonic vibration element A3 is arranged on a lower portion of the fitting grooves 9a, 10a and the ultrasonic vibration receiving element A4 is arranged on the lid member H adapted to be positioned above the fitting grooves 9a, 10a.

The ultrasonic wave is irradiated by the ultrasonic vibration element A3 on the flexible tubes forming the arterial blood circuit 1 and the venous blood circuit 2 fitted in the fitting grooves 9a, 10a and the vibrations of the flexible tubes are received by the ultrasonic vibration receiving element A4. The ultrasonic vibration receiving element A4 can vary its output voltage according to received vibrations. That is, since the damping factor of ultrasonic wave of the air-bubbles is higher than those of the blood or the substitution solution, a fact that a voltage detected by the ultrasonic vibration receiving element A4 exceeds a predetermined threshold means that any air-bubble has passed through the arterial blood circuit 1 and the venous blood circuit 2.

According to the structure described above, it is possible to complete or interrupt the dialysis treatment by dosing the electromagnetic valves 11, 12 when the blood discriminating means 13, 14 detected that liquid flowing through the predetermined position has substituted by the substitution solution from blood or when the air-bubble detecting means 15, 16 has detected any flow of air bubbles through the arterial blood circuit 1 and the venous blood circuit 2.

The main body 8 of the dialysis apparatus contains the recognition means 17, the control means 18, the monitoring means 19 and an informing means 20. The recognition means 17 is formed e.g. by a microcomputer or part thereof and able to recognize a "final stage of blood-return" which means a state near the completion of substitution of blood by physiological saline according to presence or absence of blood detected by the blood discriminating means 13, 14. In the present invention, the "final stage of blood-return" includes not only just before the end of blood-return but the latter half of actually required blood-return time duration (after intermediate time of blood-return).

The control means 18 is formed e.g. by a microcomputer or part thereof electrically connected to the recognition means 17 and able to perform predetermined controls relating to actions or operations carried out in the final stage of blood-return subject to recognition of the final stage of blood-return by the recognition means 17. More particularly, the control means 18 of the present embodiment can perform a control of increase or decrease of supplying flow rate of the physiological saline (substitution solution) by the substitution solution supplying means (saline bag 7 and substitution solution supplying line Lc) subject to recognition of the final stage of blood-return by the recognition means 17 as well as a control of intermittent supply of the physiological saline (substitution solution) by the substitution solution supplying mean subject to recognition of the final stage of blood-return by the recognition means 17.

This makes it possible to vary the supplying flow rate of the physiological saline between points of time of the final stage of blood-return and of blood-return prior to this by increasing or decreasing the supplying flow rate of the physiological saline (substitution solution) by the substitution solution supplying means subject to recognition of the final stage of blood-return by the recognition means 17, and thus to control the supplying flow rate of the physiological saline according to the degree of progress of blood-return. Especially, when reducing the supplying flow rate of the substitution solution (physiological saline) by the substitution solution supplying means subject to the recognition of the final stage of blood-return by the recognition means 17, it is possible to suppress sudden elevation of blood pressure of a patient in the final stage of blood-return.

In addition, it is possible to keep thrombus or air-bubbles in their staying position by intermittently supplying the substitution solution and substituting blood by the substitution solution subject to the recognition of the final stage of blood-return by the recognition means 17. According to the present embodiment, it is possible to repeatingly drive and stop the blood pump 4 and to intermittently perform supply of the physiological saline (substitution solution) by the substitution solution supplying means.

Furthermore, the control means 18 of the present embodiment can perform the supply of the substitution solution by the substitution solution supplying means (saline bag 7 and substitution solution supplying line Lc) by a set-up amount depending on the arranged position of the detecting means (blood discriminating means 13, 14 of the arterial unit 9 and venous unit 10) subject to the recognition of the final stage of blood-return by the recognition means 17. More particularly, physiological saline is supplied by the set-up amount after recognition of the final stage of blood-return by the recognition means 17 with previously grasping a volume of the flow path from the predetermined position at which the arterial unit 9 is arranged to the tip end "a" of the arterial blood circuit 1, and a volume of the flow path from the predetermined position at which the venous unit 10 is arranged to the tip end "b" of the venous blood circuit 2 and determining these volumes as the set-up amount. This makes it possible to optimize the amount of the substitution solution in accordance with blood concentration of individual patient.

The monitoring means 19 is formed e.g. by a microcomputer or part thereof for monitoring abnormalities in the blood-return. Examples of abnormalities in the blood-return are cases in which air-bubbles are detected by the air-bubble detecting means 15, 16, venous pressure detected by the pressure sensor P exceeds a threshold etc. The monitoring means 19 of the present embodiment can monitor the abnormalities (detection of air-bubbles, abnormal pressure in the blood circuit) in real time not only in blood-return but also in blood purification treatment (dialysis treatment).

The informing means 20 can perform information by outputting voices or sound effects or displaying characters or pictures on a monitor (e.g. touch panel etc. provided on the main body 8 of the dialysis apparatus) to inform medical workers information by outputting an alarm when any abnormality is detected by monitoring means 19 during the blood purification treatment (dialysis treatment) or blood-return.

Then, a control during the blood return in the blood purification apparatus of the first embodiment of the present invention will be described with reference to a flowchart of FIG. 7. The opening/closing means 21 is opened and the blood pump 4 is driven to a normal or reverse direction according to electric signals from the main body 8 of the dialysis apparatus when the blood-return is started after completion of the blood purification treatment (step S1). The supplying flow rate of the physiological saline supplied to the blood circuit is determined by the driving speed of the blood pump 4. Blood-return of venous blood circuit 2 can be performed by closing the electromagnetic valve 11 and opening the electromagnetic valve 12 when the blood pump 4 is driven to the normal direction, and on the other hand, blood-return of arterial blood circuit 1 can be performed by opening the electromagnetic valve 11 and closing the electromagnetic valve 12 when the blood pump 4 is driven to the reverse direction.

Then it is discriminated whether the physiological saline (substitution solution) is detected by the blood discriminating means 13, 14 (strictly speaking, detection of blood is disappeared) (step S2). When it is discriminated that the physiological saline is detected, the "final stage of blood-return" (i.e. state near completion of the substitution by physiological solution) is recognized by the recognition means 17 and then goes to a step S3. In the step S3, change of supplying flow rate or intermittent supply of the physiological saline (substitution solution) is performed.

That is, subject to recognition of the final stage of blood-return by the recognition means 17, controls for increasing or decreasing the supplying flow rate of the physiological saline (substitution solution) by the substitution solution supplying means (the saline bag 7 and the substitution solution supplying line Lc) or for intermittently supplying the physiological saline by the substitution solution supplying means are performed. Alternately, it may be possible to perform either one of the change of the supplying flow rate or intermittent supply of the physiological saline (substitution solution), or perform these controls simultaneously or sequentially.

Then, supply of the physiological saline (substitution solution) is performed (step S4) by a set-up amount depending on the arranged position (the predetermined position at which the arterial unit 9 and venous unit 10 are arranged) of the blood discriminating means 13, 14 (detecting means). According to the present embodiment, the set-up amount is a volume of the flow path from the predetermined position at which the arterial unit 9 is arranged to the tip end "a" of the arterial blood circuit 1, or a volume of the flow path from the predetermined position at which the venous unit 10 is arranged to the tip end "b" of the venous blood circuit 2. The blood pump 4 is stopped at a point of time when the supply of the substitution solution reached the set-up amount. A series of blood-return operations are ended when the substitution of blood with the substitution solution is completed in both the arterial blood circuit 1 and the venous blood circuit 2.

In place of the manner described above in which the physiological saline (substitution solution) is supplied by the set-up amount after recognition of the final stage of blood-return by the recognition means 17, it may be possible to supply the substitution solution by a predetermined amount to constant volume irrespective of a volume of the flow paths from the predetermined position at which the arterial unit 9 and the venous unit 10 are arranged to the tip ends "a" and "b" of the arterial blood circuit 1 and the venous blood circuit 2) subject to the recognition of the final stage of blood-return by the recognition means 17.

According to the first embodiment of the present invention described above, since the control means 18 can increase or decrease a supplying flow rate of the substitution solution (physiological saline) by the substitution solution supplying means subject to the recognition of the final stage of blood-return by the recognition means 17, it is possible to make the supplying flow rate of the substitution solution suitable for the final stage of blood-return. Especially, when reducing the supplying flow rate of the substitution solution (physiological saline) by the substitution solution supplying means subject to the recognition of the final stage of blood-return by the recognition means 17, it is possible to suppress sudden elevation of blood pressure of a patient in the final stage of blood-return.

Further according to the first embodiment of the present invention, since the control means 18 can intermittently perform the supply of the substitution solution by the substitution solution supplying means subject to the recognition of the final stage of blood-return by the recognition means 17, it is possible to suppress thrombus or air-bubbles stayed in the blood circuit from being carried to a body of patient. In addition, since the control means 18 can perform the supply of the substitution solution by the substitution solution supplying means by a set-up amount depending on the arranged position of the detecting means (blood discriminating means 13, 14) subject to the recognition of the final stage of blood-return by the recognition means 17, it is possible to reduce use of the substitution solution (physiological saline).

Although it is described that the blood discriminating means 13, 14 as detecting means are arranged on both the arterial blood circuit 1 and the venous blood circuit 2 respectively, the blood discriminating means may be arranged only either one of the arterial blood circuit 1 or the venous blood circuit 2. Also, in the embodiment described above, the blood discriminating means 13, 14 as detecting means are arranged in the arterial unit 9 and the venous unit 10 respectively. However, the blood discriminating means 13, 14 may be arranged in an arbitrary position other than the tip end side position of the arterial blood circuit 1 and the venous blood circuit 2.

Then a blood purification apparatus of a second embodiment of the present invention will be described. Similarly to the first embodiment, the blood purification apparatus of this embodiment including a dialysis apparatus for performing dialysis treatment mainly comprises a blood circuit including an arterial blood circuit 1 and a venous blood circuit 2; a dialyzer (blood purification means) 3; a blood pump 4; an arterial air-trap chamber 5 and a venous air-trap chamber 6; a main body 8 of the dialysis apparatus; a saline bag 7 and a substitution solution supplying line Lc forming a substitution solution supplying means; blood discriminating means 13, 14 forming a blood detecting means; a recognition means 17; a control means 18; and a monitoring means 19. Same reference numerals are used herein for designating same structural elements of the first embodiment.

A main structure and functions of the monitoring means 19 of the second embodiment is substantially same as those of the first embodiment, however the monitoring means 19 of this embodiment is different from that of the first embodiment in that it has stepwise levels (alarm ranges or thresholds to be judged as abnormal) in abnormality monitoring and that it can be set at an arbitrary monitoring level. For example, when monitoring whether an bubbles have been detected by the air-bubble detected means 15, 16, air-bubbles can be detected when a voltage detected by the ultrasonic vibration receiving element A4 exceeds a predetermined threshold. Accordingly, it is possible according to this embodiment to set the monitoring level at a high threshold level (loose monitoring level) and a low threshold level (severe monitoring level). The monitoring level can be switched.

In addition, for example, when monitoring whether there is an abnormality in the venous blood pressure detected by the pressure sensor P, clogging of flow path in the arterial blood circuit 1 and the venous blood circuit 2 can be detected when the venous pressure detected by the pressure sensor P exceeds a predetermined threshold. Accordingly, in the present embodiment, it is possible to set and switch the monitoring levels at a high threshold level (loose monitoring level) and a low threshold level (severe monitoring level).

As described above, although the monitoring means 19 can monitor abnormalities in blood-return (detection of air-bubbles or abnormal venous pressure) at plural monitoring levels not limited to two monitoring levels described above, it is possible to monitor other abnormalities, more particularly to detect abnormalities by monitoring detected values relating to pressures during blood-return.

According to this embodiment, the monitoring level of the monitoring means 19 is set at the loose monitoring level when the blood-return is started and changed to the severe monitoring level by the control means 18 subject to recognition of the final stage of blood-return by the recognition means 17. That is, the control means 18 of this embodiment is configured so that the monitoring means 19 performs severe monitoring subject to recognition of the final stage of blood-return by the recognition means 17.

Then, a control during the blood-return in the blood purification apparatus of the second embodiment of the present invention will be described with reference to a flowchart of FIG. 8. The opening/closing means 21 is opened and the blood pump 4 is driven to a normal or reverse direction according to electric signals from the main body 8 of the dialysis apparatus when the blood-return is started after completion of the blood purification treatment (step S1). The supplying flow rate of the physiological saline supplied to the blood circuit is determined by the driving speed of the blood pump 4. The monitoring level of the monitoring means 19 is set at a previously determined level (relatively loose monitoring level) (step S2).

Then it is discriminated whether the physiological saline (substitution solution) is detected by the blood discriminating means 13, 14 (strictly speaking, detection of blood is disappeared) (step S3). When it is discriminated that the physiological saline is detected, the "final stage of blood-return" (i.e. state near completion of the substitution by physiological solution) is recognized by the recognition means 17 and then goes to a step S4. In the step S4, change of the monitoring level of the monitoring means 19 to a relatively severe level is performed and thus monitoring of abnormality is made severe.

Then, supply of the physiological saline (substitution solution) is performed (step S5) by a set-up amount depending on the arranged position (the predetermined position at which the arterial unit 9 and venous unit 10 are arranged) of the blood discriminating means 13, 14 (detecting means). According to the present embodiment, the set-up amount is a volume of the flow path from the predetermined position at which the arterial unit 9 is arranged to the tip end "a" of the arterial blood circuit 1, or a volume of the flow path from the predetermined position at which the venous unit 10 is arranged to the tip end "b" of the venous blood circuit 2. The blood pump 4 is stopped at a point of time when the supply of the substitution solution reached the set-up amount. A series of blood-return operations are ended when the substitution of blood with the substitution solution is completed in both the arterial blood circuit 1 and the venous blood circuit 2.

Similarly to the first embodiment, in place of the manner described above in which the physiological saline (substitution solution) is supplied by the set-up amount after recognition of the final stage of blood-return by the recognition means 17, it may be possible to supply the substitution solution by a predetermined amount (a constant volume irrespective of a volume of the flow paths from the predetermined position at which the arterial unit 9 and the venous unit 10 are arranged to the tip ends "a" and "b" of the arterial blood circuit 1 and the venous blood circuit 2) subject to the recognition of the final stage of blood-return by the recognition means 17.

According to the second embodiment of the present invention, since the blood purification apparatus comprises a monitoring means 19, and the control means 18 can make the abnormality monitoring by the monitoring means 19 severe subject to the recognition of the final stage of blood-return by the recognition means 17, it is possible to more surely suppress thrombus or air-bubbles stayed in the blood circuit from being carried to a body of patient. In this case, it is preferable to construct the blood purification apparatus so that the informing means 20 automatically performs information of an abnormality and the control means 18 automatically stop the blood-return operation when any abnormality is detected by the monitoring means 19.

Then a blood purification apparatus of a third embodiment of the present invention will be described. Similarly to the first and second embodiments, the blood purification apparatus including a dialysis apparatus for performing dialysis treatment mainly comprises a blood circuit including an arterial blood circuit 1 and a venous blood circuit 2; a dialyzer (blood purification means) 3; a blood pump 4; an arterial air-trap chamber 5 and a venous air-trap chamber 6; a main body 8 of the dialysis apparatus; a saline bag 7 and a substitution solution supplying line Lc forming a substitution solution supplying means; blood discriminating means 13, 14 forming a blood detecting means; a recognition means 17; a control means 18; and a monitoring means 19. Same reference numerals are used herein for designating same structural elements of the first and second embodiment.

The main structure and function of the informing means 20 of this embodiment are substantially same as those of the first embodiment, however the informing means 20 of this embodiment can perform information of medication to a patient. For example, when medication to a patient together with blood is required during the blood-return by introducing a predetermined medicine to the blood circuit (mainly venous blood circuit 2), the informing means 20 can perform information that a predetermined medication should be performed to a patient subject to the recognition of the final stage of blood-return by the recognition means 17 according to this embodiment.

Then, a control during the blood-return in the blood purification apparatus of the third embodiment of the present invention will be described with reference to a flowchart of FIG. 9. The opening/closing means 21 is opened and the blood pump 4 is driven to a normal or reverse direction according to electric signals from the main body 8 of the dialysis apparatus when the blood-return is started after completion of the blood purification treatment (step S1). The supplying flow rate of the physiological saline supplied to the blood circuit is determined by the driving speed of the blood pump 4.

Then it is discriminated whether the physiological saline (substitution solution) is detected by the blood discriminating means 13, 14 (strictly speaking, detection of blood is disappeared) (step S2). When it is discriminated that the physiological saline is detected, the "final stage of blood-return" (i.e. state near completion of the substitution by physiological solution) is recognized by the recognition means 17 and then goes to a step S3. In the step S3, information of performing a predetermined medication to a patient is generated under the control of the control means 18.

After information of medication, it is judged whether the medication has performed (S4). For example, it is possible to provide an operation means (e.g. operation button or touch panel) to be operated by medical workers when medication has been completed so as to judge whether the medication has been completed by a fact of operation of the operating means. When it is judged that the medication has been performed at step S4, supply of the physiological saline (substitution solution) is performed (step S5) by a set-up amount depending on the arranged position (the predetermined position at which the arterial unit 9 and venous unit 10 are arranged) of the blood discriminating means 13, 14 (detecting means). According to the present embodiment, the set-up amount is a volume of the flow path from the predetermined position at which the arterial unit 9 is arranged to the tip end "a" of the arterial blood circuit 1, or a volume of the flow path from the predetermined position at which the venous unit 10 is arranged to the tip end "b" of the venous blood circuit 2. The blood pump 4 is stopped at a point of time when the supply of the substitution solution reached the set-up amount. A series of blood-return operations are ended when the substitution of blood with the substitution solution is completed in both the arterial blood circuit 1 and the venous blood circuit 2.

Similarly to the first embodiment, in place of the manner described above in which the physiological saline (substitution solution) is supplied by the set-up amount after recognition of the final stage of blood-return by the recognition means 17, it may be possible to supply the substitution solution by a predetermined amount (a constant volume irrespective of a volume of the flow paths from the predetermined position at which the arterial unit 9 and the venous unit 10 are arranged to the tip ends "a" and "b" of the arterial blood circuit 1 and the venous blood circuit 2) subject to the recognition of the final stage of blood-return by the recognition means 17.

On the other hand, when it is not judged that the medication has performed at step S4, after predetermined time duration lapsed (S6), supplying flow rate of the physiological saline (substitution solution) is reduced by reducing driving speed of the blood pump 4 (step S7). Then, a certain reminder (e.g. repeating information by the informing means 20) is made (step S8) and the blood pump 4 is stopped with giving a predetermined alarm (step S9). Accordingly, it is impossible to advance the process to a condition waiting for medication with stopping (or interrupting) the blood-return.

According to the third embodiment, since the control means 18 can perform information that medication to a patient should be performed to a patient subject to the recognition of the final stage of blood-return by the recognition means 17, it is possible to prevent that medical workers forget medication to be performed at the final stage of blood-return and thus possible to surely perform necessary medication. Although the information of medication is performed by the informing means 20 in this embodiment, it may be performed by any other separate informing means.

In addition, according to this embodiment, the control means 18 makes information by the informing means 20 that medication to a patient should be performed subject to the recognition of the final stage of blood-return by the recognition means 17. However, the control means 18 is also possible to make the informing means 20 inform other medical treatment to be performed at the final stage of blood-return such as blood collection or measurement of blood pressure or pulse, etc. This makes it possible to prevent that medical workers forget the predetermined treatments to be performed at the final stage of blood-return and thus possible to surely perform necessary medical treatments.

Then, a control during the blood-return in the blood purification apparatus of the fourth embodiment of the present invention will be described with reference to a flowchart of FIG. 10. The opening/closing means 21 is opened and the blood pump 4 is driven to a normal or reverse direction according to electric signals from the main body 8 of the dialysis apparatus when the blood-return is started after completion of the blood purification treatment (step S1). The supplying flow rate of the physiological saline supplied to the blood circuit is determined by the driving speed of the blood pump 4.

Then it is discriminated whether the physiological saline (substitution solution) is detected by the blood discriminating means 13, 14 (strictly speaking, detection of blood is disappeared) (step S2). When it is discriminated that the physiological saline is detected, the "final stage of blood-return" (i.e. state near completion of the substitution by physiological solution) is recognized by the recognition means 17 and then goes to a step S3. In the step S3, supply of the physiological saline (substitution solution) is performed by a set-up amount depending on the arranged position (the predetermined position at which the arterial unit 9 and venous unit 10 are arranged) of the blood discriminating means 13, 14 (detecting means).

In particular, physiological saline is supplied by the set-up amount after recognition of the final stage of blood-return by the recognition means 17 with previously grasping a volume of the flow path from the predetermined position at which the arterial unit 9 is arranged to the tip end "a" of the arterial blood circuit 1, and a volume of the flow path from the predetermined position at which the venous unit 10 is arranged to the tip end "b" of the venous blood circuit 2 and determining these volumes as the set-up amount.

According to the fourth embodiment, since the control means 18 can perform the supply of the substitution solution (physiological saline) by the substitution solution supplying means by a set-up amount depending on the arranged position (the predetermined position at which the arterial unit 9 and venous unit 10 are arranged) of the blood discriminating means (detecting means) 13, 14 subject to the recognition of the final stage of blood-return by the recognition means, it is possible to reduce use of the substitution solution. Thus it is possible to optimize amount of substitution solution in accordance with blood concentration of an individual patient.

As described above, according to the first to fourth embodiments of the present invention, since the blood purification apparatus of the present invention comprises the detecting means 13, 14 arranged at predetermined positions in the arterial blood circuit 1 and the venous blood circuit 2 and detecting presence or absence of the blood flowing in the arterial blood circuit 1 and the venous blood circuit 2 at said predetermined positions, and the recognition means 17 for recognize a final stage of blood-return which is a condition near the end of the substitution of blood with the substitution solution (physiological saline) based on the presence or absence of the blood or blood concentration detected by the detecting means 13, 14, it is possible to perform actions and operations in accordance with the final stage of blood-return.

Further according to the first to fourth embodiments of the present invention, since the blood purification apparatus comprises a control means 18 for performing predetermined controls concerning to actions or operations carried out at the final stage of blood-return subject to the recognition of the final stage of blood-return by the recognition means 17, it is possible to automatically perform actions and operations according to final stage of the blood-stage. In addition, since the detecting means is a blood discriminating means 13, 14 which is arranged at predetermined positions in tip end sides "a" and "b" of the arterial blood circuit 1 and the venous blood circuit 2 and can discriminate presence or absence of the blood flowing in the arterial blood circuit 1 and the venous blood circuit 2 at said predetermined positions, it is possible to divert the blood discriminating means used during medical treatment to the detecting means.

The present invention has been described with reference to the preferred embodiments. Obviously, modifications and alternations will occur to those of ordinary skill in the art upon reading and understanding the preceding detailed description. For example, it is possible to replace the detecting means comprising blood discriminating means 13, 14 with a blood concentration sensor (e.g. hematocrit sensor) for detecting the concentration of blood flowing through the arterial blood circuit 1 or the venous blood circuit 2. The hematocrit sensor is possible to detect the blood concentration in real time.

In other embodiment, it is possible to construct the recognition means so that it can recognize the final stage of blood-return with grasping state of progress of substitution by physiological saline according to blood concentration detected by a blood concentration sensor. This makes it possible to perform stepwise controls (e.g. severely increase the monitoring level in stepwise) during the final stage of blood-return and thus to perform stepwise controls according to state of progress of the blood-return.

Also in other embodiment, it is possible to construct the recognition means so that it can recognize the early stage of blood-return in addition to the final stage of blood-return so as to make supplying flow rate of the substitution solution in the early stage of blood-return higher than that in the final stage of blood-return, in this case, the time duration of blood-return can be reduced by increasing the supplying flow rate of the substitution solution in the early stage of blood-return and sudden elevation of blood pressure of a patient can be suppressed by reducing the supplying flow rate of the substitution solution in the final stage of blood-return.

Although it is described that the control means 18 independently performs controls relating to actions or operations shown in the first to fourth embodiments subject to recognition of the final stage of blood-return by the recognition means 17 according to blood concentration detected by the detecting means comprising the blood discriminating means 13, 14, blood concentration sensor, etc. it may be possible to simultaneously perform these controls in an arbitrary combination.

In addition, although it is described in the embodiments that the substitution solution supplying means is formed by the saline bag 7 and the substitution solution supplying line Lc and the physiological saline as substitution solution is supplied to the blood circuit by driving the blood pump 4, the present invention is not limited to such a structure and it is possible to use dialysate as substitution solution during blood-return e.g. by reversely filtering dialysate from the dialysate-side flow paths to the blood-side flow paths in the dialyzer 3. The substitution solution used in the blood-return is not limited to physiological saline and dialysate and other substitution solution may be used.

Finally although it is described in the embodiments of the present invention that the control means 18 can perform various controls subject to recognition of the final stage of blood-return by the recognition means 17, the information can be performed by simply indicating the "final stage of blood-return". In this case, a medical worker can manually perform operations necessary for the final stage of blood-return. Although it is described that the blood purification apparatus of the present invention is applied to a dialysis apparatus used in dialysis treatment, it may be applied to other apparatus (such as a blood filtrating dialysis method, a blood filtrating method, a blood purification apparatus used in AFBF, a plasma adsorption apparatus, etc.) which can purify blood of a patient while extracorporeally circulating the blood.

APPLICABILITY IN INDUSTRIES

The present invention can be applied to any other applications if the blood purification apparatus comprises a detecting means arranged at predetermined positions in the arterial blood circuit and the venous blood circuit and detecting presence or absence or blood concentration of the blood flowing in the arterial blood circuit and the venous blood circuit at said predetermined positions, and a recognition means for recognize a final stage of blood-return which is a condition near the end of the substitution of blood with the substitution solution based on the presence or absence of the blood or blood concentration detected by the detecting means.

EXPLANATION OF REFERENCE NUMERALS 1 arterial blood circuit
2 venous blood circuit
3 dialyzer (blood purification means)
4 blood pump
5 arterial air trap chamber
6 venous air trap chamber
7 saline bag
8 main body of dialysis apparatus
9 arterial unit
10 venous unit
11, 12 electromagnetic valve
13, 14 blood discriminating means (detecting means)
15, 16 air-bubble detecting means
17 recognition means
18 control means
19 monitoring means
20 informing means

What is claimed is:
1. A blood purification apparatus comprising:
a blood circuit including an arterial blood circuit and a venous blood circuit for extracorporeally circulating blood of a patient from a tip end (a) of the arterial blood circuit to a tip end (b) of the venous blood circuit;
a blood purification means arranged between the arterial blood circuit and the venous blood circuit of the blood circuit and purifying blood flowing through the blood circuit;
a substitution solution supplying means for supplying substitution solution to the blood circuit; and
performing blood-return by substituting the blood in the blood circuit with the substitution solution supplied from the substitution solution supplying means after the blood purification treatment characterized in that the blood purification apparatus further comprises:
a detecting means arranged at predetermined positions in the arterial blood circuit and the venous blood circuit and detecting presence or absence or blood concentration of the blood flowing in the arterial blood circuit and the venous blood circuit at said predetermined positions;
a recognition means for recognizing a final stage of blood-return which is a condition near the end of the substitution of blood with the substitution solution based on the presence or absence of the blood or blood concentration detected by the detecting means; and
wherein the blood purification apparatus further comprises a control means including a microcomputer or part thereof electrically connected to the recognition means and wherein the control means performs predetermined controls concerning actions or operations carried out at the final stage of blood-return subject to the recognition of the final stage of blood-return by the recognition means; and
wherein the control means increases or decreases a supplying flow rate of the substitution solution by the substitution solution supplying means subject to the recognition of the final stage of blood-return by the recognition means.

2. The blood purification apparatus of claim 1, wherein the control means intermittently performs the supply of the substitution solution by the substitution solution supplying means subject to the recognition of the final stage of blood-return by the recognition means.

3. The blood purification apparatus of claim 1, wherein the control means performs the supply of the substitution solution by the substitution solution supplying means by a set-up amount depending on the arranged position of the detecting means subject to the recognition of the final stage of blood-return by the recognition means.

4. The blood purification apparatus of claim 1, wherein the blood purification apparatus further comprises a monitoring means for monitoring abnormalities during the blood-return, and wherein the control means sets the abnormality monitoring by the monitoring means at a severe monitoring level subject to the recognition of the final stage of blood-return by the recognition means.

5. The blood purification apparatus of claim 1, wherein the control means provides information that a predetermined medical treatment should be performed for a patient subject to the recognition of the final stage of blood-return by the recognition means.

6. The blood purification apparatus of claim 5, wherein the predetermined medical treatment is medication to a patient.

7. The blood purification apparatus of claim 1, wherein the detecting means is a blood discriminating means which is arranged at predetermined positions in tip end sides of the arterial blood circuit and the venous blood circuit and discriminates presence or absence of the blood flowing in the arterial blood circuit and the venous blood circuit at said predetermined positions.

8. The blood purification apparatus of claim 1, wherein the detecting means comprises a concentration sensor which detects the blood concentration of the blood flowing in the arterial blood circuit and the venous blood circuit at said predetermined positions, and wherein the recognition means recognizes the final stage of blood-return according to a degree of progress of the substitution by the substitution solution based on the blood concentration detected by the concentration sensor.

9. The blood purification apparatus of claim 8, wherein the recognition means recognizes an early stage of blood-return in addition to the final stage of blood-return based on the blood concentration detected by the concentration sensor, and wherein the supplying flow rate of the substitution solution supplied by the substitution solution supplying means is set larger in the early stage of blood-return than the supplying flow rate in the final stage of blood-return.

10. The blood purification apparatus of claim 4, wherein the detecting means is a blood discriminating means which is arranged at predetermined positions in tip end sides of the arterial blood circuit and the venous blood circuit and discriminates presence or absence of the blood flowing in the arterial blood circuit and the venous blood circuit at said predetermined positions.

11. The blood purification apparatus of claim 10, wherein the control means provides information that a predetermined medical treatment should be performed for a patient subject to the recognition of the final stage of blood-return by the recognition means.

12. The blood purification apparatus of claim 11, wherein the detecting means comprises a concentration sensor which detects the blood concentration of the blood flowing in the arterial blood circuit and the venous blood circuit at said predetermined positions, and wherein the recognition means is configured to recognizes the final stage of blood-return according to a degree of progress of the substitution by the substitution solution based on the blood concentration detected by the concentration sensor.

13. The blood purification apparatus of claim 1, wherein the blood purification apparatus further comprises an air-bubble detecting means arranged at predetermined positions in the arterial blood circuit and the venous blood circuit and detecting any flow of air bubbles through the arterial blood circuit and the venous blood circuit.

14. The blood purification apparatus of claim 13, wherein the air-bubble detecting means includes an ultrasonic vibration element and ultrasonic vibration receiving element.

15. The blood purification apparatus of claim 1, wherein the control means performs at least two or more of the following:
  intermittently performs the supply of the substitution solution by the substitution solution supplying means subject to the recognition of the final stage of blood-return by the recognition means;
  performs the supply of the substitution solution by the substitution solution supplying means by a set-up amount depending on the arranged position of the detecting means subject to the recognition of the final stage of blood-return by the recognition means; and
  provides information that a predetermined medical treatment should be performed for a patient subject to the recognition of the final stage of blood-return by the recognition means.

16. The blood purification apparatus of claim 1, wherein the detecting means includes a light emitting element and a light receiving element and wherein the light receiving element varies an output voltage according to its light income and discriminates presence or absence of blood flowing in the arterial blood circuit and the venous blood circuit according to detected output voltage.

17. The blood purification apparatus of claim 16, wherein the light emitting element and the light receiving element are arranged opposing each other across a fitting groove so that light irradiated on flexible tubes forming the arterial blood circuit and the venous blood circuit by the light emitting element is received by the light receiving element.

18. The blood purification apparatus of claim 8, wherein the concentration sensor is a hematocrit sensor.

19. The blood purification apparatus of claim 4, wherein the blood purification apparatus further comprises an informing means and wherein the informing means is configured to output voices or sound effects or display characters or pictures on a monitor to inform of any abnormality detected by the monitoring means.

20. The blood purification apparatus of claim 1, wherein the blood purification apparatus includes an arterial unit comprising an electromagnetic valve, the blood discriminating means and an air-bubble detecting means arranged on a predetermined position in the tip end side of the arterial blood circuit and a venous unit comprising an electromagnetic valve, the blood discriminating means and an air-bubble detecting means arranged on a predetermined position in the tip end side of the venous blood circuit; and wherein the arterial unit includes a fitting groove configured to fit at least a portion of the arterial blood circuit and the venous unit includes a fitting groove configured to fit at least a portion of the venous blood circuit.

* * * * *